United States Patent [19]

Kincaid et al.

[11] Patent Number: 5,382,443
[45] Date of Patent: Jan. 17, 1995

[54] READY-TO-EAT CEREALS CONTAINING EXTRUDED PRE-WETTED PSYLLIUM

[75] Inventors: James G. Kincaid; Michael W. Talbot, both of Battle Creek, Mich.

[73] Assignee: Kellogg Company, Battle Creek, Mich.

[21] Appl. No.: 123,352

[22] Filed: Sep. 17, 1993

[51] Int. Cl.⁶ .................. A23L 1/0526; A23L 1/164
[52] U.S. Cl. ............................. 426/620; 426/573; 426/621
[58] Field of Search ............... 426/620, 621, 619, 573

[56] References Cited

U.S. PATENT DOCUMENTS

| | | | |
|---|---|---|---|
| 3,148,114 | 9/1964 | Fahrenbach | 167/55 |
| 3,574,634 | 4/1971 | Singer | 99/83 |
| 4,348,379 | 9/1982 | Kowalsky et al. | 424/34 |
| 4,766,004 | 8/1988 | Moskowitz | 426/658 |
| 4,849,222 | 7/1989 | Broaddus | 424/195 |
| 5,024,996 | 6/1991 | Ringe | 514/57 |
| 5,026,689 | 6/1991 | Ringe et al. | 514/57 |
| 5,176,936 | 1/1993 | Creighton et al. | 426/618 |
| 5,223,298 | 6/1993 | Wullschleger et al. | 426/549 |
| 5,227,248 | 7/1993 | Wullschleger et al. | 426/549 |

*Primary Examiner*—Donald E. Czaja
*Assistant Examiner*—Mary S. Mims
*Attorney, Agent, or Firm*—Felfe & Lynch

[57] ABSTRACT

Ready-to-eat cereals containing psyllium are described. The cereals contain psyllium which has been extruded and prewetted, that is, admixed with water prior to mixing with other cereal ingredients. The prewetted psyllium, when combined with the other ingredients, yields a ready-to-eat cereal which has organoleptic properties superior to similar cereals where the psyllium has not been so treated. The cereals of the invention are particularly useful in lowering the serum cholesterol levels of individuals who consume them. Preferred cereals include ingredients such as wheat, corn or oat flours. Preferred forms of the cereals include flakes, puffs, nuggets, shreds, buds, and biscuits.

21 Claims, 3 Drawing Sheets

READY-TO-EAT CEREALS CONTAINING EXTRUDED PRE-WETTED PSYLLIUM

FIELD OF THE INVENTION

This invention relates to ready-to-eat cereals. More particularly, it relates to such cereals which contain psyllium. This psyllium contained in the cereals has been treated before incorporation into the cereal product in that it has been extruded and then prewetted. The ready-to-eat cereals containing the thus pretreated psyllium have organoleptic properties which are superior to cereal products containing psyllium which have not been so treated.

BACKGROUND AND PRIOR ART

Psyllium is a known mucilaginous material which has found extensive use in bulk laxatives. The source of psyllium is seeds from the plants of the Plantago genus, which grow in certain sub-tropical regions. The seeds are dark brown, smooth, boat-shaped and shiny. Since it is believed by those skilled in the art that the active ingredient of psyllium is the psyllium seed gum, which is located primarily in the seed husk, present technology uses the ground seed husk as the source for psyllium. However, the whole seed is also known as a psyllium source, as well as the dehusked psyllium seed.

Due to the mucilaginous nature of psyllium, however, psyllium acquires a slimy or adhesive texture and mouthfeel upon hydration. This slimy mouthfeel is unpalatable and, accordingly, various additives have been incorporated in psyllium-containing ingestible compositions in order to mask the undesirable texture and mouthfeel of the psyllium. In addition, psyllium develops a distinctive, undesirable flavor in the presence of heat and moisture which further limits its use in food products.

Notwithstanding the undesirable flavor and texture imparted to an ingestible composition by psyllium or psyllium husks, various psyllium-containing foodstuffs have been proposed which purport to take advantage of the natural digestion regulation properties of psyllium, or the satiating or "fullness-feeling" effect of psyllium. See, for example, U.S. Pat. Nos. 3,574,634 and 4,348,379.

In addition, it has been suggested, for example, in U.S. Pat. No. 3,148,114, the whole psyllium husks, such as the ground husks of the seed of Plantago psyllium, lower blood cholesterol upon oral administration thereof. Further, it has also long been known to use small quantities of psyllium, such as less than 1%, as a thickener in foodstuffs, such as in ice cream, puddings and the like.

Finally, U.S. Pat. No. 4,849,222 discloses a medicament composition for reducing blood cholesterol levels in humans and lower animals which comprises a mixture of psyllium seed gum, or source of psyllium seed gum, and a nonabsorbable, nondigestible polyol polyester.

However, as set forth above, the mucilaginous nature of psyllium husks presents grave processing difficulties, and prior attempts to produce a palatable, ready-to-eat food product containing psyllium have not resulted in a satisfactory product to date, particularly, with respect to flavor and texture or mouthfeel.

Attempts have been made to incorporate psyllium into foodstuffs, so that the fiber can be consumed as part of a regular meal or other aspect of a normal diet, without any connotation or association with medicines, as well as with acceptable organoleptic properties. Examples of the patent literature involving psyllium incorporated into foodstuffs are U.S. Pat. Nos. 5,223,298 and 5,227,248, both of which are incorporated by reference. These patents teach psyllium containing ready-to-eat cereals. Additional examples of cereals containing psyllium are set forth by Moskowitz, U.S. Pat. No. 4,766,004; Ringe U.S. Pat. No. 5,024,996; and Ringe et al., U.S. Pat. No. 5,026,689. Other foodstuffs which include psyllium are taught in U.S. Pat. Nos. 5,095,008 and 4,950,140 both of which teach cookies with incorporated psyllium, U.S. Pat. No. 5,015,486, which teaches microwavable muffins, and U.S. Pat. No. 5,024,996 in which teaches almond paste containing compositions, such as marzipan. Ready-to-eat cereals are ideal food products for incorporating materials such as psyllium, given consumer acceptance of high fiber materials in such products. In applications Ser. Nos. 08/123,353, 08/123,342, and 08/123,557 concurrently filed and assigned to the assignee of the subject application, new food products are taught, including bread, pasta, and snack bars.

It has now been found that ready-to-eat cereals and other products containing psyllium having superior organoleptic properties can be prepared. These products contain psyllium which has been extruded and prewetted prior to incorporation into the cereal product. The manner in which this is done, as well as the resulting products are subjects of this invention. Additionally, the use of the cereal products for serum cholesterol reduction is another feature of the invention.

The description which follows presents the invention in more detail.

DETAILED DESCRIPTION OF PREFERRED EMBODIMENTS

Figure 1:
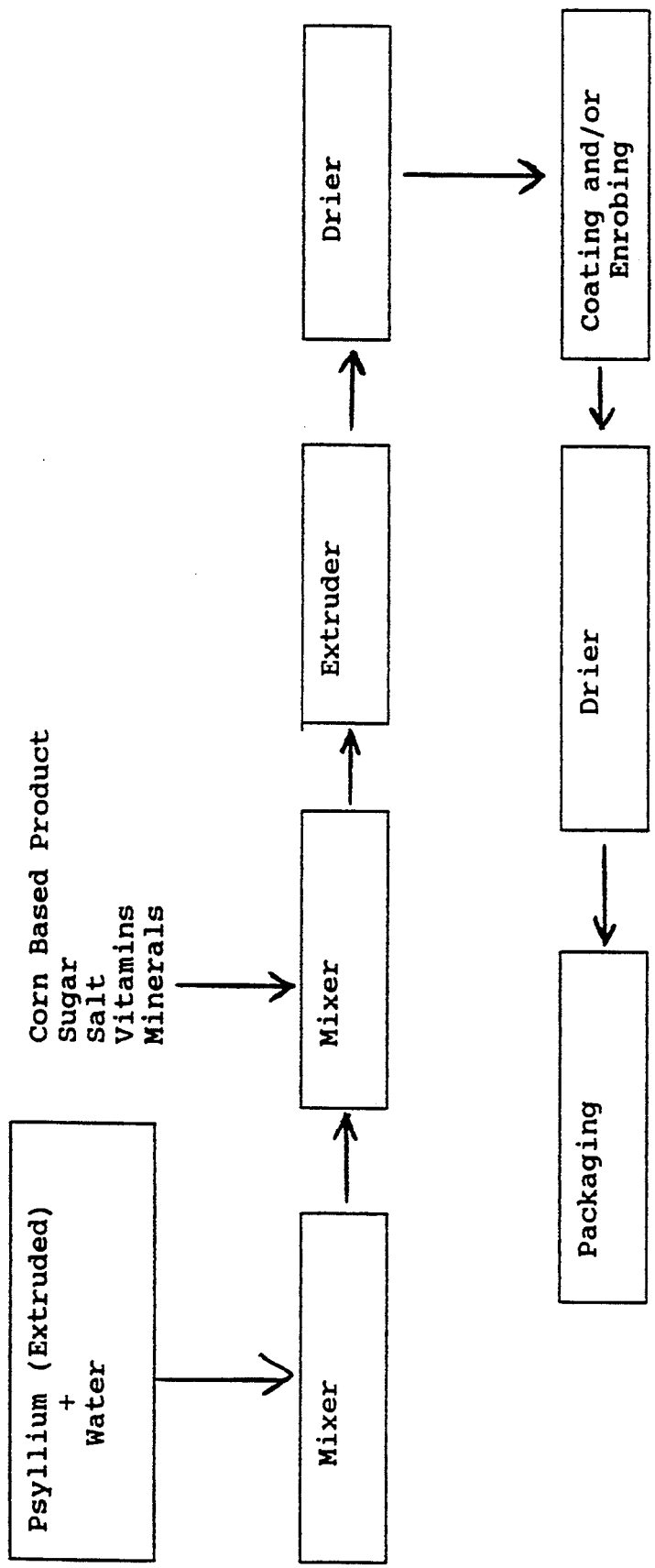
FIG. 1 sets forth a block diagram of the manufacturing process by which some of the cereal products of the present invention may be made.
Figure 2:
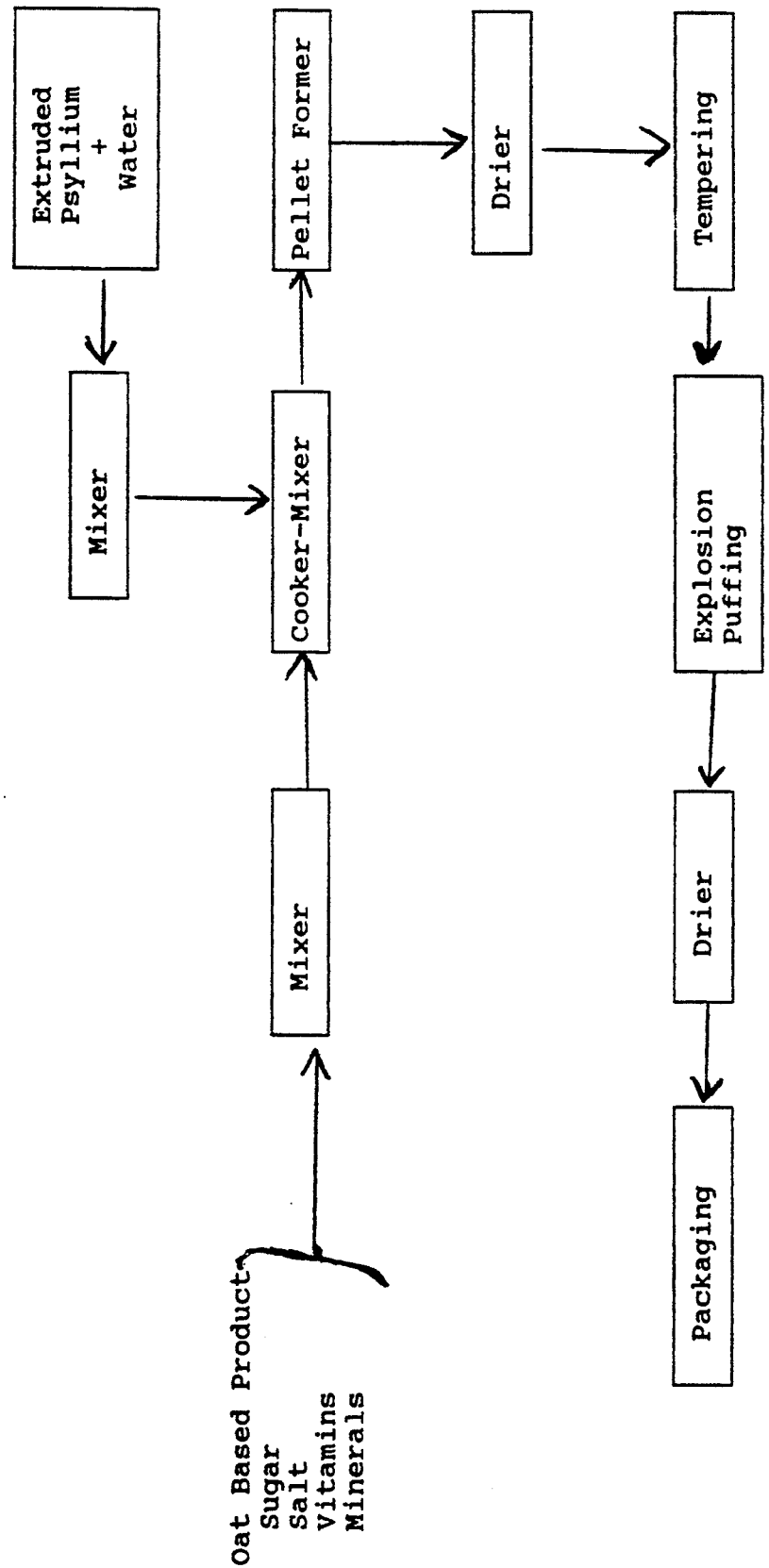
FIG. 2 presents another block diagram showing an alternate manufacturing process for making additional cereal products in accordance with the invention.
Figure 3:
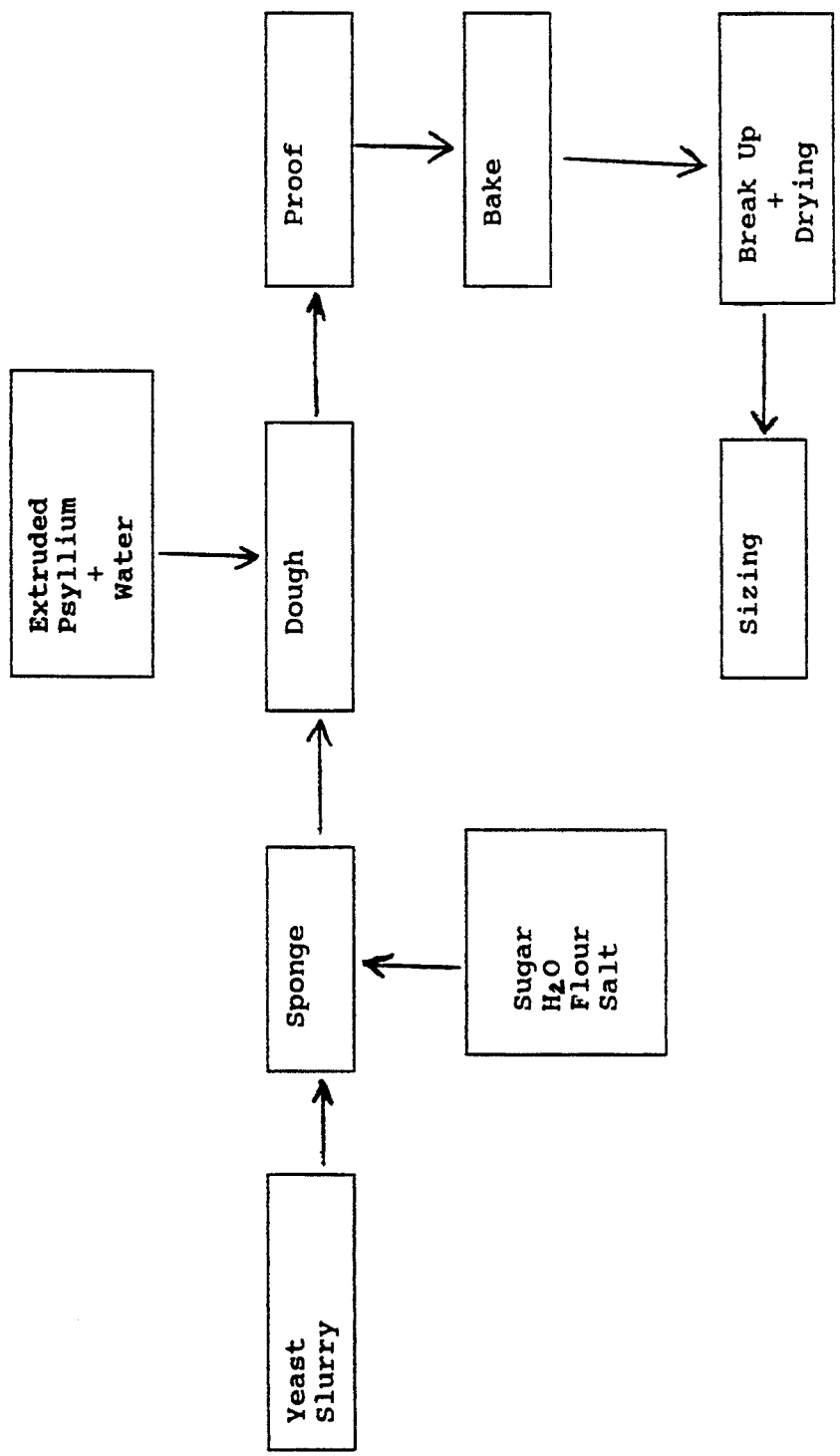
FIG. 3 depicts another diagram for producing cereals in accordance with the invention.

In the following controls and examples, reference is made to extruded psyllium, psyllium extrusion product, and so forth. The psyllium extrusion products are preferably 98% pure psyllium, and when "psyllium" is used generically, this is in fact what is meant. This material was prepared by introducing psyllium to an extruder, operating under a set of conditions which include a torque minimum of 60% a temperature of at least 240° F., and targeted screw speed of 250 rpm. The psyllium is fed into the extruder at a rate of 16.5 kg/minute, ±5%. Water is present in the extruder in an amount ranging from 15.5 to 17.5% by weight, referring to the amount of psyllium used. The psyllium is extruded through a die, and then dried at a temperature of 150°±30° F. The resulting product is cooled to 37° C. at a maximum, and has a final moisture content of from 6–10%.

Control 1

A corn based psyllium containing cereal product was made as follows.

As psyllium starting material, extruded, sterilized, psyllium husks were used. The husks were sterilized by well known sterilization procedures, and a small amount of citric acid (about 1.5 percent by weight) was added. The psyllium was then extruded as described supra to produce a psyllium extrusion product. The extruded psyllium was used in the following cereal formulation.

| Ingredient | Percent By Weight |
|---|---|
| Corn Meal | 31.39027 |
| Oat Flour | 30.49079 |
| Sucrose | 13.62999 |
| Psyllium (as above) | 11.98241 |
| Oat Bran | 10.32575 |
| Flour Salt | 0.93593 |
| Kaomel, Vegetable Oil, Flakes | 0.99953 |
| Sodium Bicarbonate | 0.22717 |
| Annatto Powder, 7.5% | 0.1817 |

The formulation was mixed in an industrial mixer, and then extruded through a standard extruder, with a die of about 0.047".

During the extrusion, water was metered in via a flow meter until the desired consistency was reached. This was determined via periodic sampling and observation of the dough product. At such point as an acceptable dough product was produced, water flow was maintained at that acceptable, minimal level. The resulting product was then coated with a coating of sugar and salt (final mixture: 96.44354% cereal product, 3.33418% sugar, 0.22228% salt). The coating was sprayed onto the cereal and was then allowed to dry.

This cereal is referred to as "product 1" in Example 3, infra.

Control 2

A second cereal product was prepared, this time not using extruded psyllium; rather, raw husk psyllium was used, (98% purity), in the same quantity as the extruded psyllium of Control 1. All other components of the cereal product were the same as product 1. The new cereal is referred to as "product 2" in the Example 3, infra.

Control 3

In this example, raw psyllium, 98% purity was ground, but not extruded. The quantities of all ingredients were the same as in Control 1 and the cereal was extruded in the same way. This yielded product 3.

EXAMPLE 1

In this example, extruded psyllium was used, as in Control 1; however, following extrusion, 13.2 pounds of psyllium were mixed with 13.2 pounds of water in a prewetting step.. The mixture of extruded psyllium was combined with the cereal ingredients of control 1, and the mixture was allowed to temper overnight. The tempered mixture was extruded, coated, and dried in the same manner as the product of "control 1". It is referred to as product 4.

EXAMPLE 2

In this example, a cereal product identical to Example 1 was prepared, except the citric acid was not included in the psyllium. In all other respects, the cereal was identical to the cereal of Example 1. This product is referred to as product 5.

EXAMPLE 3

Products 1–5 were submitted to a panel of taste testers. Each was given an equal amount of each of products 1–5, and then asked to rank these in order of preference. The results are as follows:

| TASTER A: | Products 4 and 5 (best) |
|---|---|
|  | Products 2 and 3 |
|  | Products 1 (worst) |
| TASTER B: | Product 4 (best) |
|  | Product 5 |
|  | Product 1 |
|  | Product 3 |
|  | Product 2 (worst) |
| TASTER C: | Product 4 (best) |
|  | Product 5 |
|  | Product 3 |
|  | Product 2 |
|  | Product 1 (worst) |
| TASTER D: | Product 4 (best) |
|  | Product 5 |
|  | Product 3 |
|  | Product 2 |
|  | Product 1 (worst) |
| TASTER E: | Product 4 (best) |
|  | Product 5 |
|  | Products 3, 2 and 1 |
| TASTER F: | Product 5 (best) |
|  | Product 3 |
|  | Product 4 |
|  | Product 2 |
|  | Product 1 (worst) |

There was a clear preference in terms of texture, appearance, color and flavor among the tasters for cereal prepared with prewet psyllium. Among the qualities which were liked by the panel were its color and crunchiness.

EXAMPLE 4

An oat cereal was prepared from the following ingredients:

| INGREDIENT | Amt(lb) | Weight Percent (Dry Basis) |
|---|---|---|
| Water | 82.2 | — |
| Oat Flour | 81.2 | 85.97449 |
| Wheat Starch | 7.1 | 7.50000 |
| Sucrose | 3.0 | 3.50000 |
| Salt | 1.9 | 2.50000 |
| $CaCO_3$ | 0.298 | 0.35000 |
| $Na_3(PO_4)$ | 0.220 | 0.25936 |
| Monoglycerides | 0.128 | 0.15000 |
| Reduced iron | 0.025 | 0.02992 |
| Niacinamide | 0.016 | 0.01828 |
| Thiamine Mononitrate | 0.012 | 0.01370 |
| Pyridoxine-HCl | 0.002 | 0.00233 |
| Riboflavin | 0.001 | 0.00155 |
| Folic acid | 0.000 | 0.00037 |

This ingredients were used as a cereal base. The flour ingredients (oat flour, wheat starch, $CaCO_3$), and water were combined, added to a mixer, and warmed to 120° F. The remaining ingredients were then added, and the mixture was mixed for 10 minutes, heated in a jacket vessel, with the jacket pressure at 40 pounds per square inch for 75 minutes, with the mixer running at 80 rpm. In the last 10 minutes of cooking, 10.5 lbs of 98% psyllium with citric acid was added, which had been prewet with 5.65 lb of water. This psyllium containing mixture was then hot pelletized, passed through a Bohler mold to form O shapes, and the cereal pieces were then dried at 220°–240° F. to a moisture content of 8% $H_2O$. The product was then puffed. The cereal product which resulted was analyzed for various nutritional components. A serving (one ounce), contained 280 mg of sodium, 2 g of fat, 1 g of sugar, 5 g of total dietary fiber, and 1 g of insoluble dietary fiber. Of this total dietary fiber 4 g was soluble fiber, ~3.0 coming from the psyllium.

EXAMPLE 5

An oat puff cereal was prepared using the following formulation:

| INGREDIENT | AMT (LB) | WEIGHT PERCENT (Dry Basis) |
|---|---|---|
| Oat Flour | 209.1 | 66.00000 |
| Wheat Starch | 69.8 | 15.44000 |
| Psyllium seed husks | 53.3 | 12.00000 |
| Sucrose | 16.0 | 4.00000 |
| Salt | 8.0 | 2.00000 |
| MYVAPLEX | 2.0 | 0.50000 |
| $Na_3PO_4$ | 0.240 | 0.06000 |
| Niacin | 0.073 | 0.01818 |
| Iron | 0.065 | 0.1636 |
| Zno | 0.027 | 0.00682 |
| Pyridoxine·HCl | 0.009 | 0.00233 |
| Riboflavin | 0.006 | 0.00155 |
| Thiamin | 0.005 | 0.00136 |
| Folic Acid | 0.001 | 0.00036 |

All ingredients were combined in a Blonco mixture, with water added in the same manner as described in Control 1 and Example 4, and mixed for 15 minutes, after which the mixture was cooked. Cooked dough was then extruded through a die (220" hole, 0.143" pin, 1/6 cutoff), and dried to a moisture content of 12%. The product was tempered overnight, puffed, and then dried.

EXAMPLE 6

A nugget cereal was prepared by combining:

| | | |
|---|---|---|
| 1. Whole wheat flour | 7.3 lb | |
| 2. Sponge | 6.6 lb | |
| 3. Salt Slurry | 2.8 lb | |
| 4. Malted Barley Flour | 1.2 lb | |
| 5. Date Paste | 1.2 lb | |
| 6. Water | 0.8 lb | |
| 7. Salt | 0.069 lb | |

The "salt slurry" was prepared by mixing 2.9 lb of water with 0.096 lb of salt.

"Sponge" was prepared by mixing 5.6 lb of water at 120° F., 4.1 lb of whole wheat flour, 0.360 lb of sugar, and 0.698 lb of a yeast slurry. The yeast slurry was prepared by mixing 0.616 lb of water at 120° F. with 0.080 lb of yeast. The flour, sugar and water were mixed in a mixer for three minutes, after which the yeast slurry was added, and mixed for five minutes. The resulting sponge was allowed to rest for 1.5 hours before use.

Ingredients "4" through "7" were combined. Then, ingredients "2" and "3" were added, and the combination mixed in a blender for two minutes. Whole wheat flour was then added slowly, and a nugget dough (about 20.2 lbs) resulted.

After the whole wheat flour was combined into the other ingredients, prewetted psyllium (3.4 lb) was added. This had been prepared by combining equal amounts of water and psyllium (10 lbs each). Once the prewetted psyllium was added, the product was mixed for 4 minutes in the mixer, using a dough hook.

The dough was proofed for one hour at room temperature, and then baked into loaves (375° F., 50 minutes). The loaves were cooled and tempered for one hour, after which they were broken into large pieces, and dried for 20 minutes at 200° F. The dried breads were comminuted through a 0.750" screen, and then dried again for 20 minutes at 200° F. They were then sized, and toasted for three minutes at 325° F. The resulting nuggets had a hard texture, which is desirable in a nugget cereal, and a good malted barley flavor.

EXAMPLE 7

The cholesterol lowering effect of the psyllium enriched snack bars of this invention is confirmed by the following study.

Over the course of six months, a long term intervention study is conducted to test the effect of the psyllium enriched product on the level of serum cholesterol on sample size of 250 hypercholesterolemic individuals. Individuals chosen for this study are at risk for mild abnormalities in their cholesterol levels. Generally, the study targets individuals with plasma LDL-cholesterol levels at 130 to 220 mg/dl, with the proviso that their triglycerides levels are less than 300 mg/dl. There is an initial eight week dietary instruction and stabilization period where lipid criteria are ascertained.

According to the protocol of the intervention study, the individuals participating in the study are divided into four groups. The groups are administered varying number of servings of a psyllium enriched food product to determine whether there is a dose dependent hypocholesterolemic effect. The participants are given a choice of psyllium enriched food products: R-T-E-cereal, bread, snack bars, and pasta, which are packaged in zero and 3 mg psyllium servings. All products are prepared in accordance with the copending applications cited supra.

Group A is given three servings of the placebo product per day and is not administered a psyllium food product at all.

Group B is given two servings of the test product and one serving of the placebo product per day.

Group C is given one serving of the test product and two servings of the placebo product per day.

Group D is given three servings of the test product per day and no placebo.

The serum cholesterol levels are tested periodically during the study by taking blood samples and determining cholesterol level in the serum.

The cholesterol levels decrease from baseline over the course of the study indicating the hypocholesterolemic effect of psyllium enriched products. The study further shows that the decrease in serum cholesterol is in proportion to the dosage units of psyllium product ingested.

The foregoing examples show that cereal products where extruded psyllium is prewetted, i.e., combined with water and possibly allowed to temper prior to admixing with other cereal ingredients have superior organoleptic properties to those preparations where the psyllium has not been prewetted. Thus, in its broadest embodiment, the invention is a ready-to-eat cereal which comprises extruded, prewetted psyllium. These ready-to-eat cereals comprise at least one cereal ingredient and at least 2% by weight of prewetted extruded psyllium.

"Cereal ingredient" as the term is used herein refers to any of the bulk cereal ingredients well known to the art as exemplified by the patents cited supra, e.g. Among the ingredients embraced thereby are whole grain products, such as corn, oats, whole wheat, barley, and rye; grain components such as the germ and/or bran of any of the aforementioned grains, the flours of these grains; starches derived therefrom, and so forth. Any edible component of the grain is embraced within the ambit of cereal ingredient and grain product. Other raw ingredients which may be included are legume products, such as soybeans, peas, beans and the like, non-bran fiber sources (prune fiber, guar, beet fiber, citrus pulp), as well as other products. Other grains, such as amaranth, quinoa, teff, buckwheat, and so forth, may also be used.

The prewetted psyllium may be prepared in any number of forms, using various psyllium containing raw ingredients. As the examples indicate, psyllium husks may be used. Similarly, psyllium may be combined with various ingredients to prepare compositions containing anywhere from 50% to 100% psyllium. As is indicated supra, one preferred embodiment of the invention employs psyllium of 98% purity. The psyllium may also be combined with preservatives such as citric acid. Thus, when "psyllium containing composition" is used herein, it refers to any composition containing anywhere from about 50% to about 100% by weight of psyllium, optionally containing a preservative, such as citric acid.

The ready-to-eat cereals of the invention may be in any of the forms in which standard breakfast cereals occur, such as flakes, puffs, shreds, buds, nuggets, biscuits, etc. These products may be coated with, e.g., sugar based materials or other coatings (e.g., fruit juice concentrates) or other materials. Any of the traditional additives to ready-to-eat cereals, such as other cereals, raisins, cranberries or other dried fruits, nuts, confectionaries such as marshmallow, and so forth, may be used.

The key ingredient in the cereals of the invention is the prewetted psyllium. Prewetted psyllium is prepared by combining psyllium with water and allowing the mixture to temper before combining with other ingredients. It is preferred to combine the water and psyllium in a ratio of from about 0.75:1 to 1.25:1 (by weight) a ratio of 1:1 being particularly preferred.

The tempering period for the prewetted psyllium may vary. The key qualities that prewetted psyllium possesses as compared to non-prewetted material is that its hygroscopicity is reduced and maintains its free flowing nature. If the prewetted material is allowed to temper for more than about 24-48 hours, this free-flowing property is lost. Further, this extensive time period may encourage the growth of microorganisms. Thus, the prewetted psyllium of the ready-to-eat cereals is not permitted to temper for more than about 24-48 hours. It is especially preferred to allow it to temper for less than about 12 hours. It is especially preferred to use the psyllium as soon as possible after wetting it. The foregoing time parameters on tempering apply when the prewetted psyllium is combined with other ingredients. As in example 1, supra, the prewetted psyllium may be combined with other ingredients and the resulting mixture allowed to temper for less than 12 hours before further processing.

The amount of prewetted psyllium in the ready-to-eat cereal may vary, with the preferred range being anywhere from about 2% to 50% by weight, a range of 2-30% being preferred. In a particularly preferred ready-to-eat cereal, the amount of prewetted psyllium may range from about 6% to about 19% by weight, a range of about 11% to about 14% being especially preferred.

The procedures by which the ready-to-eat cereals of the invention are made are also a part of the invention. These processes require the combining of extruded psyllium with water for a tempering period, as described above. Following the tempering period, the psyllium, which is referred to herein as prewetted psyllium, is combined with the chosen cereal ingredients, to form a cereal product. This cereal product is then treated to produce the final product, i.e., the ready-to-eat cereal. The treating of the product may involve any of a number of steps. For example, the product can be extruded and dried, and then optionally coated with a coating agent, such as is described in Example 1. It may also be flaked, optionally in a rippled or other textured form, puffed or expanded, shredded, formed into biscuits, dried, and so forth. In addition, if necessary or desirable, the cereal product may be cooked prior to any subsequent treating steps. A cooking step may be used when the cereal ingredient is one where digestibility and/or polatability is improved by cooking, such as oats.

The cereal product described supra may also be further combined with other ingredients to form additional products which are not necessarily ready-to-eat cereals. The cereal product may be used, e.g., in connection with other ingredients to form mixes for quick breads and other similar materials, such as pancakes, waffles, scones, muffins, and so forth, as well as in other grain based products. The manner in which these products are prepared follows standard procedures well known to the art, and as such they are not elaborated upon herein.

The ready-to-eat cereals and other materials discussed and described herein may be used in any of the ways psyllium containing products have been used in the art. For example, these products have been used as diet regulating agents, as laxatives, and as sources of fiber in a diet. They are especially useful, however, in reduction of serum cholesterol levels, as the discussion of the references cited supra will show. Thus, yet another aspect of the invention is a method for reducing serum cholesterol levels in a subject via consumption of the described cereal products.

Other aspects of the invention will be evident to the skilled artisan and need not be elaborated upon herein.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:
1. Ready-to-eat (R-T-E) cereal products comprising:
   (i) at least one cereal ingredient, and
   (ii) at least 2% by dry weight of extruded, prewetted psyllium.
2. The ready-to-eat cereal product of claim 1, wherein said cereal ingredient is an edible corn product.

3. The ready-to-eat cereal of claim 2, wherein said edible corn product is whole corn, corn meal, corn flour, corn grits, corn starch, corn bran or corn germ.

4. The ready-to-eat cereal of claim 1, wherein said extruded, prewetted psyllium is present in an amount ranging from about 6% to about 19% by dry weight.

5. The ready-to-eat cereal of claim 4, wherein said extruded, prewetted psyllium is present in an amount ranging from about 11% to about 14% by dry weight.

6. The ready-to-eat cereal product of claim 1, wherein said cereal ingredient is an edible oat product.

7. The ready-to-eat cereal product of claim 6, wherein said oat product is oat meal, oat flour, oat bran, whole oats, oat fiber, rolled oats, steel cut oats, oat fiber or oat germ.

8. The ready-to-eat cereal product of claim 1, in the form of a flake, a puff, a nugget, a shred, a bud or a biscuit.

9. The ready-to-eat cereal product of claim 8, in the form of a nugget.

10. Extruded, prewetted psyllium containing composition.

11. The extruded prewetted psyllium containing composition of claim 10, further comprising citric acid.

12. Process for making a ready-to-eat cereal, comprising:
   (i) mixing extruded psyllium with water to form prewetted psyllium;
   (ii) combining the prewetted psyllium with at least one bulk cereal ingredient to form a cereal mixture;
   (iii) tempering the cereal mixture for a time period not to exceed twelve hours, and;
   (iv) forming said cereal mixture into a ready-to-eat cereal product.

13. The process of claim 12, wherein said forming comprises extruding said cereal mixture to form an extruded product and drying said extruded product.

14. The process of claim 12, further comprising cooking said cereal mixture prior to said forming step.

15. Ready-to-eat (R-T-E) cereal produced by the process of claim 12.

16. Ready-to-eat (R-T-E) cereal produced by the process of claim 13.

17. Ready-to-eat (R-T-E) cereal produced by the process of claim 14.

18. Method for reducing serum cholesterol in a subject comprising administering to said subject an amount of the ready-to-eat cereal product of claim 1 sufficient to reduce the serum cholesterol level of said subject.

19. Process for making a psyllium product useful for incorporating in a food product, comprising:
   (i) extruding a psyllium containing composition;
   (ii) mixing the extruded psyllium containing composition with water, and; (iii) tempering the mixture of the psyllium containing composition and water for a period of time less than 12 hours.

20. The process of claim 1, wherein said water is mixed with said psyllium in an amount which ranges from about 75% to about 125% by weight of the amount of psyllium with which it is mixed.

21. Process of claim 19, further comprising combining the mixture of extruded psyllium containing composition and water with a cereal ingredient prior to tempering.

* * * * *